(12) United States Patent
Tanabe et al.

(10) Patent No.: US 6,348,189 B1
(45) Date of Patent: *Feb. 19, 2002

(54) HAIR CLEANSING COMPOSITIONS CONTAINING GLYCINE AND ALANINE

(75) Inventors: Hisateru Tanabe; Masato Oshika; Shinobu Nagase; Satoshi Shibuichi; Kenji Arai, all of Tokyo (JP)

(73) Assignee: Kao Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/465,448

(22) Filed: Dec. 17, 1999

(30) Foreign Application Priority Data

Dec. 28, 1998 (JP) .............................. 10-374707
Jan. 26, 1999 (JP) .............................. 11-017493

(51) Int. Cl.[7] .............................. A61K 7/08; A61K 7/06; A61K 7/075

(52) U.S. Cl. .............. 424/70.24; 424/70.1; 424/70.11; 424/70.12; 424/70.22; 510/119; 510/127

(58) Field of Search .............. 424/70.1, 70.12, 424/70.22, 70.13, 70.24, 70.11; 510/119, 127

(56) References Cited

U.S. PATENT DOCUMENTS 5,712,232 A    1/1998   Moriyama et al.
6,228,353 B1 * 5/2001   Carr et al.

FOREIGN PATENT DOCUMENTS

| EP | 0 186 025 | | 7/1986 |
|---|---|---|---|
| GB | 1 401 089 | * | 7/1975 |
| GB | 2 322 550 | | 9/1998 |
| JP | 10-236927 | | 9/1998 |
| WO | 98/29094 | | 7/1998 |

OTHER PUBLICATIONS

S.V. Brodin et al., Chemical Abstracts, AN 126 : 45358, "Metabolism of [2–14C] Glycine in Tissues of Rats in Vivo", 1996.

S. I. Vovk, et al.,Chemical Abstracts, AN 119 : 25240, "Use of [U–14C] Leucine, [U–14C] Alanine, and [U–14C] Glucose in Synthesis of Lipids in Lamb Tissues Under in Vivo Conditions", 1993.

V. M. Grigorev, et al.,Chemical Abstracts, AN 123: 338057, "Food and Cosmetic Additives Containing Mineral and Trace Elements and Carboxylic Acids", May 27, 1995.

* cited by examiner

*Primary Examiner*—Thurman K. Page
*Assistant Examiner*—Brian K. Seidleck
(74) *Attorney, Agent, or Firm*—Oblon, Spivak, McClelland, Maier & Neustadt, P.C.

(57) ABSTRACT

This invention relates to a hair cleansing composition, which comprises (A) 0.01 to 20 wt. % of glycine or alanine, (B) 0.01 to 5 wt. % of an α-hydroxy acid, β-hydroxy acid, 1,2-dicarboxylic acid, 1,3-dicarboxylic acid or aromatic carboxylic acid, and (C) 5 to 40 wt. % of an anionic surfactant selected from an alkylsulfuric acid salt, an alkylethersulfuric acid salt or an N-alkylamidoalkanolsulfuric acid ester salt. The hair cleansing composition is excellent in the effect of improving optical or mechanical properties of hair.

6 Claims, No Drawings

HAIR CLEANSING COMPOSITIONS CONTAINING GLYCINE AND ALANINE

TECHNICAL FIELD

This invention relates to a hair cleansing composition excellent in the effect of improving optical or mechanical properties of hair.

BACKGROUND ART

Concerning conventional hair cleansing compositions, their effect of improving optical or mechanical properties of hair, such as luster, softness, body and the like, is either temporary or insufficient.

JP 10-236927 A discloses a hair treatment composition for supplying a precursor of a hair-united lipofatty acid to hair follicles, in which (i) a first fatty acid precursor selected from leucine, isoleucine, methionine or valine, (ii) a second fatty acid precursor selected from a saccharide or a mono-, di- or tri-carboxylic acid and (iii) an anionic, amphoteric or cationic surfactant has been added. However, this invention was created by drawing a hint from the fact that the above-described components (i) and (ii) act as a precursor of a hair-united lipofatty acid for hair follicles. It is therefore impossible to predict from this invention what components should be added for the improvement of optical or mechanical properties of hair.

The present invention therefore has as an object the provision of a hair cleansing composition excellent in the effect of improving optical or mechanical properties of hair.

DISCLOSURE OF THE INVENTION

The present inventors have found that combined use of glycine or alanine and a specific acid compound with an anionic surfactant at a particular ratio makes it possible to obtain a hair cleansing composition excellent in the effect of improving optical or mechanical properties of hair such luster, softness, body and the like.

This invention therefore provides a hair cleansing composition comprising the following components:

| | |
|---|---|
| (A) glycine or alanine | 0.01 to 20 wt. % |
| (B) α-hydroxy acid, β-hydroxy acid, 1,2-dicarboxylic acid, 1,3-dicarboxylic acid or aromatic carboxylic acid | 0.01 to 5 wt. % |
| (C) an anionic surfactant selected from alkylsulfuric acid salt, alkylethersulfuric acid salt or N-alkylamido-alkanolsulfuric acid ester salt. | 5 to 40 wt. % |

BEST MODE FOR CARRYING OUT THE INVENTION

The component (A) for use in the present invention is glycine or alanine of these, particularly preferred are glycine and α-alanine.

As the component (A), glycine and alanine may be used in combination. The component (A) is added in a proportion of from 0.01 to 20 wt. %, preferably from 0.05 to 10 wt. %, notably from 0.1 to 5 wt. % based on the whole composition. This range is preferred in imparting color deepness to hair.

Among acids usable as the component (B) in the present invention, illustrative a-hydroxy acids and β-hydroxy acids can include glycolic acid, lactic acid, methylacetic acid, mandelic acid, 4-hydroxymandelic acid, 3-hydroxy-4-methoxymandelic acid, 4-hydroxy-3-methoxymandelic acid, 3-(2-hydroxyphenyl)lactic acid, 3-(4'-hydroxyphenyl) lactic acid, 3,4-dihydromandelic acid, glyceric acid, malic acid, tartaric acid, and citric acid.

Further, illustrative 1,2-dicarboxylic acids and 1,3-dicarboxylic acids can include malonic acid, succinic acid, maleic acid, and fumaric acid. Illustrative aromatic carboxylic acids can include benzoic acid, phthalic acid, and salicylic acid.

Among these, malic acid, succinic acid and maleic acid are particularly preferred.

As the component (B), one or more of the above-described acids can be used. The component (B) is added in a proportion of from 0.01 to 5 wt. %, preferably from 0.05 to 3 wt. %, notably from 0.1 to 2 wt. % based on the whole composition. This range is preferred in imparting transparency to hair.

The anionic surfactant for use as the component (C) in the present invention is selected from alkylsulfuric acid salts, alkylethersulfuric acid salts and N-alkylamidoalkanolsulfuric acid ester salts. Surfactants tants other than these anionic surfactants cannot provide foam in sufficient volume so that no softness can be imparted to hair upon foaming.

Of these, particularly preferred are alkylsulfuric acid salts containing alkyl groups of 10 to 16 carbon atoms, polyoxyethylene alkylethersulfuric acid salts containing alkyl groups of 10 to 20 carbon atoms and added with 1 to 5 moles on average of ethylene oxide in the molecule, and N-alkylamidoalkanolsulfuric ester salts represented by the following formula (1):

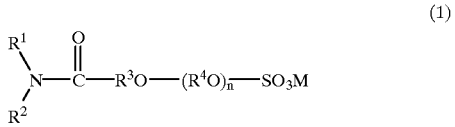

$$\begin{array}{c}R^1\\ \diagdown\\ N-C-R^3O-(R^4O)_n-SO_3M\\ \diagup\\ R^2\end{array} \qquad (1)$$

wherein $R^1$ represents an alkyl or alkenyl group having 6 to 22 carbon atoms, $R^2$ represents an alkyl or alkenyl group having 1 to 22 carbon atoms or a hydrogen atom, $R^3$ represents an alkylene group having 1 to 5 carbon atoms, $R^4O$ represents an oxyalkylene group having 2 to 3 carbon atoms, n stands for a number of from 0 to 20, n $R^4Os$ may be the same or different, and M represents a hydrogen atom, an alkali metal, an alkaline earth metal, an ammonium group, an alkanolammonium group having 2 to 9 carbon atoms in total, an alkylammonium or alkenylammonium group having 1 to 22 carbon atoms in total, an alkyl- or alkenyl-substituted pyridinium group, said alkyl or alkenyl having 1 to 18 carbon atoms, or a basic amino acid residue.

These anionic surfactants may be used either singly or in combination. The anionic surfactant is added in a proportion of from 5 to 40 wt. %, preferably from 5 to 30 wt. %, notably from 10 to 20 wt. % based on the whole composition. A proportion smaller than 5 wt. % cannot provide sufficient cleansing power, while a proportion greater than 40 wt. % cannot provide an adequate viscosity.

To the hair cleansing composition according to the present invention, (D) a cationic polymer can be added further. This cationic polymer can improve the manageability and touch of hair further.

Illustrative of the cationic polymer are cationized cellulose derivatives, cationic starch, cationized guar gum derivatives, homopolymers of diallyl quaternary ammonium salts, diallyl quaternary ammonium salt/acrylamide copolymers, quaternized polyvinylpyrrolidone derivatives, polyglycolpolyamine condensation products, vinylimidazolium trichloride/vinylpyrrolidone copolymer, hydroxyethylcellulose/dimethyl diallyl ammonium chloride copolymer, vinylpyrrolidone/quaternized dimethylaminoethyl methacrylate copolymers, polyvinylpyrrolidone/alkyl aminoacrylate copolymers, polyvinylpyrrolidone/alkyl aminoacrylate/vinylcaprolactam copolymers, vinylpyrrolidone/methacrylamidopropylchlorotrimethyl ammonium copolymer, alkylacrylamide/acrylate/alylaminoalkylacrylamide/polyethylene glycol methacrylate copolymers, adipic acid/dimethylaminohydroxypropylethylenetriamine copolymer ("Cartaretin", trade mark; product of Sandoz Chemical Corp., U.S.A.), and cationic polymers disclosed in JP 53-139734 A and JP 60-36407.

Among these, cationized cellulose derivatives are preferred.

These cationic polymers may be used either singly or in combination. The cationic polymer is added in a proportion of from 0.01 to 5 wt. %, preferably from 0.05 to 2 wt. %, notably from 0.1 to 1 wt. % based on the whole composition.

To the hair cleansing composition according to the present invention, (E) a silicone can be added further. This silicone can provide hair with nongreasiness.

Preferred examples of the silicone are methyl-siloxanes represented by the following formula (2):

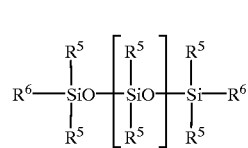

(2)

wherein $R^5$ represents a methyl or phenyl group, $R^6$ represents a methyl or hydroxyl group, and m stands for a number of from 100 to 2,000.

These silicones may be used either singly or in combination. The silicone is added in a proportion of from 0.01 to 10 wt. %, preferably from 0.1 to 5 wt. %, notably 0.5 to 3 wt. % based on the whole composition.

To the hair cleansing composition according to the present invention, surfactants other than those described above, cosmetic oils, dyes, reducing agents, oxidizing agents, metal chelates, antioxidants, viscosity modifiers, preservatives, animal and plant extracts, antiphlogistics, disinfectants, antidandruff agents, oxidation inhibitors, pearlants, ultraviolet absorbers, pH regulators, colors, solvent, perfumes and the like can be added as desired in addition to the above-described components.

The pH of the hair cleansing composition according to the present invention may preferably range from 2 to 12, with pH 4 to 8 being particularly preferred.

The hair cleansing composition according to the present invention can be produced by an ordinary method and can be used, for example, as a shampoo or dry shampoo.

EXAMPLE 1

Shampoos were prepared by mixing their corresponding components shown in Table 1, and the external appearance, softness/body, manageability and touch of hair when the shampoos were used were ranked. In each ranking, permed and bleached hair samples were used. The results are also presented in Table 1.

(Ranking method)

After bundles of hair, each of which was 20 cm in length and 10 g in weight, were washed with a commercial shampoo ("Lavenus Cleansing Shampoo", trade mark; product of Kao Corp.), 3-gram portions of the individual shampoos were applied to the bundles of hair, respectively. After the bundles of hair were left over for 30 minutes, the shampoos were caused to foam and the bundles of hair were then rinsed with warm water of 40° C. Subsequent to drying, they were organoleptically ranked in comparison with untreated bundles of hair by ten expert panellers in accordance with the following ranking standards.

| <External appearance of hair> | |
|---|---|
| Deep in luster and color, high transparency, and shiny | +1 point |
| Cannot be said good or bad | 0 point |
| Lackluster, timid color, no transparency, and dry and loose | −1 point |

Based on the total points of all the panellers, each sample acquired +4 points or more was ranked "A", each sample acquired +3 to −3 points was ranked "B", and each sample acquired −4 point or less was ranked "C".

| | |
|---|---|
| Adequate resiliency touch and good body | +1 point |
| Can be said neither | 0 point |
| Soft and silky touch | −1 point |

Based on the total points of all the panelists, each sample acquiring +4 points was ranked "A", each sample acquiring +3 to −3 points was ranked "B" and each sample acquiring −4 points or less was ranked "C".

| <Manageability of hair> | |
|---|---|
| Well managed without hair out of place | +1 point |
| Cannot be said good or bad | 0 point |
| Not managed with hair out out of place | −1 point |

Based on the total points of all the panellers, each sample acquired +4 points or more was ranked "A", each sample acquired +3 to −3 points was ranked "B", and each sample acquired −4 point or less was ranked "C".

| <Touch> | |
|---|---|
| Silky touch | +1 point |
| Cannot be said good or bad | 0 point |
| No silky touch | −1 point |

Based on the total points of all the panellers, each sample acquired +4 points or more was ranked "A", each sample acquired +3 to −3 points was ranked "B", and each sample acquired −4 point or less was ranked "C".

TABLE 1

| | Invention product | | | | | Comparative product | | |
|---|---|---|---|---|---|---|---|---|
| Component (wt. %) | 1 | 2 | 3 | 4 | 5 | 1 | 2 | 3 |
| Sodium POE (2.0) dodecylsulfate | 15.0 | 15.0 | 15.0 | 15.0 | 15.0 | 15.0 | 15.0 | 15.0 |
| Chloro-O-[2-(hydroxy-3-(trimethylammonio)-propyl]hydroxyethylcellulose | 0.5 | | 0.5 | 0.5 | 0.5 | | 0.5 | 0.5 |
| Glycine | 1.0 | 2.0 | 1.0 | 1.0 | | | | 0.5 |
| α-Alanine | | | | | 1.0 | | | |
| Malic acid | 0.5 | 0.5 | | | 0.5 | | 0.5 | |
| Maleic acid | | | 0.5 | | | | | |
| Succinic acid | | | | 0.5 | | | | |
| pH regulator (HCl) | | | | | | q.s. | q.s. | q.s |
| pH regulator (NaOH) | q.s | q.s. | q.s. | q.s. | q.s. | q.s. | q.s. | q.s |
| Perfume | 0.5 | 0.5 | 0.5 | 0.5 | 0.5 | 0.5 | 0.5 | 0.5 |
| Water | Balance | Balance | Balance | Balance | Balance | Balance | Balance | Balance |
| pH | 5.5 | 5.5 | 5.5 | 5.5 | 5.5 | 5.5 | 5.5 | 5.5 |
| Hair external appearance | A | A | A | A | A | C | B | C |
| Softening/body | C | C | C | C | A | B | A | C |
| Hair manageability | A | A | A | A | A | C | C | B |
| Touch | A | A | A | A | A | C | B | B |

EXAMPLE 2

Shampoos (Invention Products 6–10; pH 5.5) were prepared in a similar manner as Invention Products 1–5 in Example 1 except that methylpolysiloxane ("KF96A 5,000 cs", trade name; product of Shin-Etsu Chemical Co., Ltd.) was additionally incorporated in a proportion of 1 wt. %.

With respect to the shampoos so obtained, their external appearance of hair, softening/body, hair manageability and touch were ranked. Invention Products ts 6–10 all gave similar results as in Example 1. In addition, they were also organoleptically ranked for the nongreasiness of hair in a similar manner as in Example 1 in accordance with the following ranking standard.

| <Nongreasiness of hair> | |
|---|---|
| Nongreasy | +1 point |
| Cannot be said good or bad | 0 point |
| Lack of nongreasiness | −1 point |

Based on the total points of all the panellers, each sample acquired +4 points or more was ranked "A", each sample acquired +3 to −3 points was ranked "B", and each sample acquired −4 point or less was ranked "C"

As a result, Invention Products 6–10 were all ranked "A" in the nongreasiness of hair.

CAPABILITY OF EXPLOITATION IN INDUSTRY

Hair cleansing compositions according to the present invention have excellent cleansing power and can significantly improve optical or mechanical properties of hair. They impart color deepness, transparency and shiny luster. They also impart softness and body to hair, so that the manageability of hair is improved.

Japanese Patent Application Nos. 10-374707 and 11-017493, filed on Dec. 28, 1998 and Jan. 26, 1999 respectively, are incorporated herein by references in there entirety.

What is claimed is:

1. A hair cleansing composition comprising:

(A) 0.01 to 20 wt. % alanine;

(B) 0.01 to 5 wt. % of an acid selected from the group consisting of malic acid, and maleic acid and a mixture thereof; and (C) 5 to 40 wt. % of an anionic surfactant selected from the group consisting of an alkylsulfuric acid salt, an alkylethersulfuric acid salt, an N-alkylamido-alkanolsulfuric acid ester salt and a mixture thereof.

2. The hair cleansing composition of claim 1, further comprising (D) a cationic polymer.

3. The hair cleansing composition of claims 1 or 2, further comprising (E) a silicone.

4. A hair cleansing composition comprising:

(A) 0.01 to 20 wt. % glycine;

(B) 0.01 to 5 wt. % of an acid selected from the group consisting of malic acid, maleic acid and a mixture thereof; and (C) 5 to 40 wt. % of an anionic surfactant selected from the group consisting of an alkylsulfuric acid salt, an alkylethersulfuric acid salt, an N-alkylamido-alkanolsulfuric acid ester salt and a mixture thereof.

5. The hair cleansing composition of claim 4, further comprising (D) a cationic polymer.

6. The hair cleansing composition of claims 4 or 5, further comprising (E) a silicone.

* * * * *